US005702948A

United States Patent [19]
Greene et al.

[11] Patent Number: 5,702,948
[45] Date of Patent: Dec. 30, 1997

[54] SACCULAR COLLAGEN AND COMPOSITIONS AND METHODS FOR MAKING AND USING THE SAME

[75] Inventors: Mark L Greene, Penn Valley; James G. Davis, Philadelphia, both of Pa.

[73] Assignee: The Trustees of the University of Pennsylvania, Philadelphia, Pa.

[21] Appl. No.: 383,744

[22] Filed: Feb. 2, 1995

[51] Int. Cl.$^6$ .................................................. C12N 15/12
[52] U.S. Cl. .................... 435/348; 435/350; 435/351; 435/352; 435/363; 435/252.3; 435/254.2; 435/320.1; 536/23.5
[58] Field of Search ................... 536/23.5; 435/320.1, 435/252.3, 255.1, 240.2, 348, 350, 351, 358, 363, 254.2

[56] References Cited

U.S. PATENT DOCUMENTS

| | | | |
|---|---|---|---|
| 4,736,866 | 4/1988 | Leder et al. | 800/1 |
| 4,873,191 | 10/1989 | Wagner et al. | 435/172.3 |
| 5,434,058 | 7/1995 | Davidson | 435/69.1 |

OTHER PUBLICATIONS

Davis, J. G. (1994) dissertation Abstracts Inter. 55 (5B), 1758.
Abe, N, et al. (1994) Biochim. et Biophy Acta 1204, 61–67.
Davis, J. G., et al. (1995) Science 267, 1031–1034.
Altschul et al., "Basic Local Alignment Search Tool", *J. Mol. Biol.* 1990, 215, 403–410.
Brass, A. et al., "The Fibrillar Collagens, Collagen VIII, Collagen X and the C1q Complement Proteins Share a Similar Domain in Their C-Terminal Non-Collagenous Regions", *FEBS* 1992, 303(2,3), 126–128.
Chomczynski, P. et al., "Single–Step Method of RNA Isolation by Acid Guanidium Thiocyanate–Phenol–Chloroform Extraction", *Analytical Biochemistry* 1987, 162, 156–159.
Corwin, J., "Postembryonic Production and Aging of Inner Ear Hair Cells in Sharks", *J. Compl. Neur.* 1981, 201, 541–553.
Fisher, C. et al., "In–situ Hybridization Using Digoxigenin Labelled Probes in Human Skin", *British J. of Dermatology* 1991, 125, 516–520.
LuValle, P. et al., "The Type X Collagen Gene. Intron Sequences Split the 5'–Untranslated Region and Separate the Coding Regions for the non–Collagenous Amino–Terminal and Triple–helical Domains", *The J. of Biol. Chem.* 1988, 263(34), 18378–18385.
Muragaki, Y. et al., "The α2 (VIII) Collagen Gene", *The J. of Biol. Chem.* 1991, 266(12), 7721–7727.

Ninomiya, Y. et al., "The Developmentally Regulated Type X Collagen Gene Contains a Long Open Reading Frame without Introns", *The J. of Biol. Chem.* 1986, 261 (11), 5041–5050.
Reid, K. et al., "Ig–Binding Domains of C1Q", *Immunology Today* 1990, 11(11), 387–38.
Simmons, D. et al., "A Complete Protocol for In Situ Hybridization of Messenger RNAs in Brain and Other Tissues With Radio–Labeled Single–Stranded RNA probes", *The J. of Histotechnology* 1989, 12(3), 169–181.
Springer, J.E. et al., "Non–Radioactive Detection of Nerve Growth Factor Receptor (NGFR) mRNA in Rat Brain using In Situ Hybridization Histochemistry", *The J. of Histochemistry and Cytochemistry* 1991, 39(2), 231–234.
Van Gelder, R. et al., "Amplified RNA Synthesized from Limited Quantities of Heterogeneous cDNA", *PNAS USA* 1990, 87, 1663–1667.
Yamaguchi, N. et al., "The α1(VIII) Collagen Gene is Homologous to the α1(X) Collagen Gene and Contains a Large Exon Encoding the Entire Triple helical and Carboxy-l–terminal Non–triple helical Domains of the α1 (VIII) Polypeptide", *The J. of Biol. Chem.* 1991, 266(7), 4508–4513.
Yamaguchi, N. et al., "The Cloning and Sequencing of α1(VIII) Collagen cDNAs Demonstrate That Type VIII Collagen is a Short Chain Collagen and Contains Triple–Helical and Carboxyl–Terminal Non–triple–helical Domains Similar to Those of Type X Collagen", *The J. of Biol. Chem.* 1989, 264, 16022–16029.
Davis, J.G. et al., "Use of the Teleost Saccule to Identify Genes Involved in Inner Ear Function", *DNA and Cell Biology* 1995, 14(10), 833–839.

*Primary Examiner*—Charles L. Patterson, Jr.
*Attorney, Agent, or Firm*—Woodcock Washburn Kurtz Mackiewicz & Norris LLP

[57] ABSTRACT

A substantially purified saccular collagen protein and compositions, including pharmaceutical compositions, that comprise the saccular collagen protein are disclosed. Methods of using the saccular collagen which comprise injecting the saccular collagen into the tissue of an individual are disclosed. Antibodies which bind to the saccular collagen protein, nucleic acid molecules which encode the saccular collagen protein, and oligonucleotides which are identical or complementary to at least a portion of the sequence that encodes the saccular collagen proteins are disclosed. Recombinant expression vector that comprise nucleic acid molecules that encode the saccular collagen protein and host cells, including the cells of transgenic animals, which comprise the recombinant expression vectors are disclosed.

23 Claims, No Drawings

SACCULAR COLLAGEN AND COMPOSITIONS AND METHODS FOR MAKING AND USING THE SAME

ACKNOWLEDGEMENT OF GOVERNMENT RIGHTS

This invention was made in part with Government support under Research training grant in neuropathobiology grant number 5 T32 NS07064-13 award by the National Institutes of Health. The Government has certain rights in this invention.

FIELD OF THE INVENTION

The present invention relates to collagen compositions that alter tissue size, shape, and/or density and to methods of making and using the same. The present invention also relates to methods of altering the size, shape, and/or density of tissue.

BACKGROUND OF THE INVENTION

Collagen is a polypeptide substance comprising one third of the total protein in mammalian organisms. It is the main constituent of skin, connective tissue, and the organic substance of bones and teeth. Collagen production in the body is preceded by the formation of a much larger molecule, the biosynthetic precursor procollagen, which is degraded by specific enzymes to form collagen.

Different types of collagen exist. They are all composed of molecules whose predominant feature is a triple helical rod or fibrillar conformation to fill in extracellular space. The amino acid sequence of the α-chain is mostly a repeating structure with glycine in every third position and proline or 4-hydroxyproline frequently proceeding the glycine residues. Slight differences in the primary structure establish the differences between the types of collagen. Collagen is differentiated from the accompanying extracellular matrix proteins, such as, for example, elastin and reticulin, by 1) its content of proline, hydroxyproline, and hydroxylysine, by 2) the absence of tryptophan and its low tyrosine and sulfur content, but particularly by 3) its high content of polar groups originating from the difunctional amino acids. The polar groups are responsible for the swelling properties leading eventually to dispersion of collagen in dilute acid. There is a need for compositions which alter tissue size, shape, and/or density. There is also a need for a method of altering tissue size, shape, and/or density.

SUMMARY OF THE INVENTION

The present invention relates to a substantially purified collagen protein that has an amino acid sequence that consists essentially of the amino acid sequence of SEQ ID NO:2.

The present invention relates to an isolated nucleic acid molecule that comprises a nucleotide sequence that encodes the collagen protein that has an amino acid sequence that consists essentially of the amino acid sequence of SEQ ID NO:2.

The present invention relates to an isolated nucleic acid molecule that comprises the nucleotide sequence of SEQ ID NO:1.

The present invention relates to an isolated nucleic acid molecule that comprises a nucleotide sequence identical or complementary to a fragment of SEQ ID NO:1 which is at least 10 nucleotides in length.

The present invention relates to a recombinant expression vector that comprises a nucleotide sequence that encodes the collagen protein that has an amino acid sequence that consists essentially of the amino acid sequence of SEQ ID NO:2.

The present invention relates to a host cell that comprises the recombinant expression vector that comprises a nucleotide sequence that encodes the collagen protein that has an amino acid sequence that consists essentially of the amino acid sequence of SEQ ID NO:2.

The present invention relates to a transgenic mammal that comprises the recombinant expression vector that comprises a nucleic acid sequence that encodes the collagen protein that has an amino acid sequence that consists essentially of the amino acid sequence of SEQ ID NO:2.

The present invention relates to an injectable pharmaceutical composition that comprises a pharmaceutically acceptable carrier and the collagen protein that has an amino acid sequence that consists essentially of the amino acid sequence of SEQ ID NO:2.

The present invention relates to a method of altering tissue size, shape, and/or density in an individual by injecting into the tissue of an individual an injectable pharmaceutical composition that comprises a pharmaceutically acceptable carrier and the collagen protein that has an amino acid sequence that consists essentially of the amino acid sequence of SEQ ID NO:2.

The present invention relates to a composition that comprises the collagen protein that has an amino acid sequence that consists essentially of the amino acid sequence of SEQ ID NO:2 free from other collagen proteins.

The present invention relates to an antibody that binds to an epitope which is present on a collagen protein that has an amino acid sequence that consists essentially of the amino acid sequence of SEQ ID NO:2.

DETAILED DESCRIPTION OF THE INVENTION

The present invention arises from the discovery of a new and useful member of the collagen protein family which is referred to herein as "saccular collagen". The collagen protein of the present invention is a small protein relative to other members of the collagen family. The collagen protein of the present invention contains 423 amino acids including a 217 amino acid collagenous domain having a structure characteristic of collagen family members that is in between a 57 amino acid N-terminal non-collagenous domain and a 149 amino acid C-terminal non-collagenous domain. The amino-terminal non-collagenous domain is unique to the collagen protein of the present invention while the carboxy-terminal non-collagenous domain contains a region that is highly homologous to the carboxy terminal non-collagenous domains of the type VIII and the type X collagen.

Of all of the extracellular matrix-situated collagens with described structural roles, the collagen of the present invention contains the smallest collagenous/triple helical domain. The supramolecular organization of saccular collagen is predicated to be an extracellular, hexagonally-specified, three dimensional matrix. It appears that this matrix, in the presence of the other glycoproteins associated with the otolithic membrane, resembles a fine gel.

The short chain collagens that includes collagen type VIII and X as well as saccular collagen have the following biomechanical properties. The three dimensional organization of matrices formed by the short chain collagens provide uniform tensilar strength and resistance to compressive forces compared to those formed by fibrillar collagens.

Similarly, the three dimensional organization of matrices formed by the short chain collagens provide uniform tensilar strength and resistance to compressive forces compared to either the loose random beaded meshwork matrices formed by collagen VI, or the random irregular meshwork matrices formed by collagen IV. The matrices formed by the short chain collagens can serve as a solute permeable, cell-impermeable barrier as exemplified by the formation of Descemet's membrane by collagen type VIII in the corneal endothelium. The consistency and form that matrices formed by short chain collagens can assume may be more stable and enduring because of its unique three-dimensional nature. The matrices formed by short chained collagens comprise a single collagenous molecule and can form spontaneously through self assembly. Therefore, they should be more easily formed, maintained, and altered than comparable compositions formed of other known collagens. Such matrices may also retain more reliable adherence to its original form.

The following properties distinguish matrices formed by the collagen of the present invention from those formed by other short chain collagens, specifically the related collagens type VIII and X. The small size of collagenous/TH domain of saccular collagen provides a more dense lattice due to more SC domains of any kind per unit volume of matrix. The result is a distinct biomechanical specification with regards to the tensilar strength and resistance to compressive forces of the matrix. In addition, the finer grain quality of saccular collagen make it more easily introduced in specific small regions and more easy to prepare and manipulate in large scale processing/handling.

As used herein, the term "saccular collagen" is meant to refer to the protein that has an amino acid sequence consisting of the amino acid sequence set forth in SEQ ID NO:2. As used herein, the term "protein that has an amino acid sequence consisting essentially of the amino acid sequence set forth in SEQ ID NO:2" is meant to refer to the saccular collagen that has an amino acid sequence that consists of the amino acid sequence set forth in SEQ ID NO:2, as well has derivative and analog proteins that have an amino acid sequence essentially identical to the amino acid sequence set forth in SEQ ID NO:2 but with conservative amino acid substitutions and/or deletions and/or insertions. Conservative amino acid sequences are well known and deletions and insertions of amino acids in a protein can be single amino acid, double amino acid or triple amino acid deletions and insertions or combinations thereof.

The present invention provides a substantially purified saccular collagen protein that has an amino acid sequence consisting essentially of the amino acid sequence of SEQ ID NO:2. In particular, the present invention relates to a substantially purified saccular collagen protein that has an amino acid sequence that consists of the amino acid sequence of SEQ ID NO:2. The saccular collagen of the present invention has been isolated and purified from natural sources, specifically from bluegill sunfish (*Lepomis macrochirus*) where it is found in supporting cells located at the outer perimeter of the saccular sensory epithelium.

The saccular collagen protein may be used in a variety of applications. Injectable pharmaceutical compositions are provided which are useful in cosmetic or reconstructive surgical procedures such as for the reduction of skin wrinkles, creases, folds and the like, as well as for the enlargement of tissue such as cosmetic and reconstructive tissue implants, particularly facial implants such as lip, cheek, chin and nose implants or body implants. The saccular collagen protein may be used in cosmetic compositions and is provided in compositions free of other collagen proteins. Moreover, saccular collagen protein may be used as fibers in sutures, in leather substitutes, as a gel in photographic emulsions, in coatings, and in food casings.

Saccular collagen of the invention can be isolated from natural sources, produced by recombinant DNA methods or synthesized by standard protein synthesis techniques.

Antibodies which specifically bind to the saccular collagen may be used to purify the protein from natural sources using well known techniques and readily available starting materials. Such antibodies may also be used to purify saccular collagen from material present when producing saccular collagen by recombinant DNA methodology. The present invention relates to an antibody that binds to an epitope which is present on a saccular collagen protein that comprises the amino acid sequence of SEQ ID NO:2. As used herein, the term "antibody" is meant to refer to complete, intact antibodies or Fab fragments and F(ab)$_2$ fragments thereof. Complete, intact antibodies include monoclonal antibodies such as murine monoclonal antibodies, chimeric antibodies and humanized antibodies. In some embodiments, the antibodies specifically bind to an epitope between amino acids 1 to 57 of SEQ ID NO:2 which is a unique portion of saccular collagen that constitutes the N-terminal globular portion of the saccular collagen molecule. In some embodiments, the antibodies specifically bind to epitopes between amino acids 275 to 423 of SEQ ID NO:2 which the C-terminal globular portion of the saccular collagen molecule. Preferably, the antibodies bind to epitopes in this region which are not found in corresponding regions of collagen VIII and X molecules. In some embodiments, antibodies bind to epitopes which include amino acids from the saccular collagen molecule at amino acid sequence 349–363 and/or 375–387. Antibodies that bind to an epitope which is present on a saccular collagen protein that has SEQ ID NO:2 are useful to isolate and purify saccular collagen that has SEQ ID NO:2 from both natural sources or recombinant expression systems using well known techniques such as affinity chromatography. Such antibodies are useful to detect the presence of such protein in a sample and to determine if cells are expressing the saccular collagen.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly for example, full length saccular collagen protein, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the saccular collagen, preferably the unique N-terminal portion of saccular collagen, the hybridoma which produces them is cultured to produce a continuous supply of antibodies.

Using standard techniques and readily available starting materials, a nucleic acid molecule that encodes saccular collagen may be isolated from a cDNA library, such as, for example, from bluegill sunfish saccular macula cDNA library, using probes which are designed using the nucleotide sequence information disclosed in SEQ ID NO:1. The present invention relates to an isolated nucleic acid molecule that comprises a nucleotide sequence that encodes the saccular collagen protein that comprises the amino acid sequence of SEQ ID NO:2. In some embodiments, the nucleic acid molecules consist of a nucleotide sequence that encodes the saccular collagen protein. In some embodiments, the nucleic acid molecules comprise the nucleotide sequence set forth in SEQ ID NO:1. In some embodiments, the nucleic acid molecules consist of the nucleotide sequence set forth in SEQ ID NO:1. The isolated nucleic acid molecules of the invention are useful to prepare constructs and recombinant expression systems for preparing the saccular collagen protein of the invention.

A cDNA library may be generated by well known techniques using supporting cells located at the outer perimeter of the saccular sensory epithelium or whole saccula macula which produce saccular collagen as starting material. cDNA made from bluegill sunfish saccular macula has been used to identify cDNA that encodes saccular collagen. It is preferred that the cDNA library be generated from supporting cells located at the outer perimeter of the saccular sensory epithelium of bluegill sunfish. For example, a cDNA clone which contains the nucleotide sequence is identified using probes that comprise at least a portion of the nucleotide sequence disclosed in SEQ ID NO:1 having at least 16 nucleotides, preferably 24 nucleotides. It is preferred that the probes comprise all or most of the nucleotide sequence disclosed in SEQ ID NO:1 between nucleotide 331 and nucleotide 501 of SEQ ID NO:1 or nucleotide 1600 and nucleotide 1839 of SEQ ID NO:1 and preferably no other nucleotide sequences. The probes are used to screen the cDNA library using standard hybridization techniques. Alternatively, genomic clones may be isolated using genomic DNA from any fish cell as a starting material. The present invention relates to isolated nucleic acid molecules that comprise a nucleotide sequence identical or complementary to a fragment of SEQ ID NO:1 which is at least 10 nucleotides. In some embodiments, the isolated nucleic acid molecules consist of a nucleotide sequence identical or complementary to a fragment of SEQ ID NO:1 which is at least 10 nucleotides. In some embodiments, the isolated nucleic acid molecules comprise or consist of a nucleotide sequence identical or complementary to a fragment of SEQ ID NO:1 which is 15–150 nucleotides. In some embodiments, the isolated nucleic acid molecules comprise or consist of a nucleotide sequence identical or complementary to a fragment of SEQ ID NO:1 which is 15–30 nucleotides. Isolated nucleic acid molecules that comprise or consist of a nucleotide sequence identical or complementary to a fragment of SEQ ID NO:1 which is at least 10 nucleotides are useful as probes for identifying genes and cDNA sequence having SEQ ID NO:1, PCR primers for amplifying genes and cDNA having SEQ ID NO:1 and antisense molecules for inhibiting transcription and translation of genes and cDNA, respectively, which encode saccular collagen having the amino acid sequence of SEQ ID NO:2.

The cDNA that encodes the saccular collagen may be used as a molecular marker in electrophoresis assays in which cDNA from a sample is separated on an electrophoresis gel and saccular collagen probes are used to identify bands which hybridize to such probes. Specifically, SEQ ID NO:1, or portions thereof, may be used as a molecular marker in electrophoresis assays in which cDNA from a sample is separated on an electrophoresis gel and saccular collagen specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes saccular collagen. Electrophoresis gels useful in such an assay include standard polyacrylamide gels as described in Sambrook et al., *Molecular Cloning a Laboratory Manual*, Second Ed. Cold Spring Harbor Press (1989) which is incorporated herein by reference.

The nucleotide sequence in SEQ ID NO:1 may be used to design probes, primers and complimentary molecules which specifically hybridize to the unique nucleotide sequences of saccular collagen. Probes, primers and complimentary molecules which specifically hybridize to nucleotide sequence that encodes saccular collagen may be designed routinely by those having ordinary skill in the art.

The present invention also includes labelled oligonucleotides which are useful as probes for performing oligonucleotide hybridization methods to identify saccular collagen. Accordingly, the present invention includes probes that can be labelled and hybridized to unique nucleotide sequences of saccular collagen. The labelled probes of the present invention are labelled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of saccular collagen.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encodes saccular collagen and insert it into an expression vector using standard techniques and readily available starting materials.

The present invention relates to a recombinant expression vector that comprises a nucleotide sequence that encodes the saccular collagen protein that comprises the amino acid sequence of SEQ ID NO:2. As used herein, the term "recombinant expression vector" is meant to refer to a plasmid, phage, viral particle or other vector which, when introduced into an appropriate host, contains the necessary genetic elements to direct expression of the coding sequence that encodes the saccular collagen of the invention. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:1. The recombinant expression vectors of the invention are useful for transforming hosts to prepare recombinant expression systems for preparing the saccular collagen protein of the invention.

The present invention relates to a host cell that comprises the recombinant expression vector that comprises a nucleotide sequence that encodes the collagen protein that comprises the amino acid sequence of SEQ ID NO:2. In some embodiments, the host cell comprises a recombinant expression vector that comprises SEQ ID NO:1. Host cells for use in well known recombinant expression systems for production of proteins are well known and readily available. Examples of host cells include bacteria cells such as *E. coli*, yeast cells such as *S. cerevisiae*, insect cells such as *S. frugiptera*, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes the collagen protein that comprises the amino acid sequence of SEQ ID NO:2. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes the saccular collagen of the invention is operably linked to a mammary cell specific promoter whereby the coding sequence is only expressed in mammary cells and the recombinant protein so expressed is recovered from the animal's milk. In some embodiments, the coding sequence that encodes the saccular collagen protein of the invention is SEQ ID NO:1.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of collagen in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (invitrogen, San Diego, Calif.) may, for example, be used for production in mammalian cells such as Chinese Hamster Ovary cells. One having ordinary skill in the art can use these commercial expression vectors and systems or others to produce saccular collagen or fragments thereof using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes saccular collagen or a fragment thereof is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate saccular collagen or fragment that is produced using such expression systems. The methods of purifying saccular collagen from natural sources using antibodies which specifically bind to saccular collagen as described above, may be equally applied to purifying saccular collagen produced by recombinant DNA methodology.

Examples of genetic constructs useful for transfecting with cells with DNA that encodes full length saccular collagen in order to express full length saccular collagen include SEQ ID NO:1 operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes full length saccular collagen from readily available starting materials. Such gene constructs are useful for the production of saccular collagen protein.

In some embodiments of the invention, transgenic non-human animals are generated. The transgenic animals according to the invention contain SEQ ID NO:1 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce the full length saccular collagen. Preferred animals are rodents, particularly goats, rats and mice.

In addition to producing these proteins by recombinant techniques, automated peptide synthesizers may also be employed to produce saccular collagen or fragments. Such techniques are well known to those having ordinary skill in the art and are useful if derivatives which have substitutions not provided for in DNA-encoded protein production.

Pharmaceutical compositions according to the invention comprise a pharmaceutically acceptable carrier in combination with saccular collagen protein or fragment. Pharmaceutical formulations for injectable collagen are well known and pharmaceutical compositions comprising saccular collagen may be routinely formulated by one having ordinary skill in the art. Suitable pharmaceutical carriers are described in *Remington's Pharmaceutical Sciences*, A. Osol, a standard reference text in this field, which is incorporated herein by reference. The present invention relates to an injectable pharmaceutical composition that comprises a pharmaceutically acceptable carrier and the collagen protein that has the amino acid sequence of SEQ ID NO:2. Some embodiments of the invention relate to injectable pharmaceutical compositions that comprise a pharmaceutically acceptable carrier and the saccular collagen protein that has an amino acid sequence that consists of SEQ ID NO:2. As discussed above, the saccular collagen of the invention may be injected into the tissue of an individual for cosmetic and/or reconstructive surgical purposes. Such injections effectively alter the size, shape and/or density of the tissue. The saccular collagen is sterile and combined with a sterile pharmaceutical carrier.

In some embodiments, for example, saccular collagen can be formulated as a solution, suspension, emulsion or lyophilized powder in association with a pharmaceutically acceptable subcutaneous vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a subcutaneous composition suitable for administration by injection is prepared by dissolving 1.5% by weight of saccular collagen in 0.9% sodium chloride solution.

An injectable composition may comprise saccular collagen in a diluting agent such as, for example, sterile water, electrolytes/dextrose, fatty oils of vegetable origin, fatty esters, or polyols, such as propylene glycol and polyethyleneglycol. The injectable must be sterile and free of pyrogens.

The pharmaceutical compositions of the present invention may be administered to an individual suffering from a variety of skin or connective tissue disorders so that tissue size, shape, and/or density will be affected. The present invention relates to a method of altering tissue size, shape, and/or density in an individual by injecting into the tissue of an individual an injectable pharmaceutical composition that comprises a pharmaceutically acceptable carrier and the saccular collagen protein that has an amino acid that consists of SEQ ID NO:2. Examples of tissue where saccular collagen may be injected include skin which is wrinkled, creased or folded, such as skin around the eyes and mouth. Saccular collagen may be injected into an individual's lips, nose, chin or cheeks. Surgical procedures for collagen injection and implantation are well known.

The present invention relates to a composition that comprises the saccular collagen protein that have an amino acid sequence that consists of SEQ ID NO:2 free from other collagen proteins. Examples of such compositions include drug delivery systems, cosmetics and foods. The saccular collagen may be combined with drugs in a drug delivery system or device including ointments, lotions and the like as well as sustained release/time release compositions. In some embodiments, the saccular collagen is combined with other compounds to produce cosmetic creams, oils, gels, powders and the like. In some embodiments, the saccular collagen is combined with food stuffs as a food ingredient.

Topical compositions preferably include lotions which may contain numerous compounds in addition to saccular collagen. Bentonite, as well as other suitable substitutes, may be included as a suspension agent. Methylcellulose or sodium carboxymethylcellulose may be included to localize and hold saccular collagen in contact with the affected site. Glycerin may be included to keep the skin moist. Alcohol may be included to aid in drying and cooling. Preservatives may be included to inhibit microbial growth. Fragrances may also be included.

EXAMPLES

Example 1

Construction of cDNA Libraries

The saccular sensory epithelium in an adult bluegill sunfish (*Lepomis macrochirus*) may contain as many as, or more, than $2 \times 10^5$ hair and supporting cells (Corwin, *J.*

*Comp. Neur.*, 1981, 201:541). Oligo-dT and random primed cDNA libraries were constructed from poly-A+ selected mRNAs. The oligo-dt primed library was constructed in λgt11 and consisted of nearly $9.6 \times 10^5$ recombinants ranging between 0.3 and 3.5 kB in length.

Example 2

Differential Screening of cDNA Libraries

Bluegill sunfish saccular macula cDNA libraries were differentially screened to identify inner ear-specific transcripts. Differential screening of an oligo-dT primed saccular macula cDNA library with labeled saccular macula and liver A+ cDNAs was performed. Briefly, differential screening was performed using $^{32}$P labeled sunfish saccular maculae and liver cDNAs that were prepared from poly-A+ RNAs and/or amplified RNAs (VanGelder et al., *Proc. Acad. Sci. U.S.A.*, 1990, 87:1663) using standard protocols (Maniatis et al., *Molecular Cloning: A Laboratory Manual*, Cold Spring Harbor Laboratory, Cold Spring Harbor, N.Y. (1982)). First strand cDNA was synthesized from a given A+ RNA or aRNA aliquot, was purified, and was then used as template in a standard random primed reaction to generate labeled cDNA probe. Recovery was on the order of $10^7$ cpm/100 ng of any of the starting RNAs per reaction. Nitrocellulose lifts (Schleicher and Schuell, Keene, N.H.) of the saccular maculae cDNA library platings were hybridized with labeled probe ($10^6$ cpm/ml) in 6X SSC/0.1% SDS/0.05X. These lifts were hybridized overnight at 60° C. After high stringency washes, the hybridized lifts were subjected to autoradiography at −70° C. Plaques corresponding to hybridization signals derived from the macula-probed lifts for a given plate that did not match with a corresponding signal on the liver-probed lifts from the corresponding plate were isolated from the library platings. cDNA inserts were isolated from purified phage preparations and ligated into pBluescript (Stratagene Cloning Systems, La Jolla, Calif.) according to standard cloning protocols (Maniatis et al., SUPRA). Sanger dideoxy chain termination sequencing was performed using the Sequencing Version 2.0 DNA Sequencing system (United States Biochemical Corp., Cleveland, Ohio). The cDNA was sequenced nearly in its entirety on both strands. Nucleotide and amino acid sequence analysis was performed with MacVector 4.0 software. Homology searches were performed with Blast search programs (Altschulet al., *J. Mol. Biol.*, 1990, 215:403).

The differential expression of the first saccule-specific cDNA was examined by northern analysis. Northern blot analysis was performed with a labeled 240 nucleotide 3' end-derived probe. Total RNAs were prepared using guanidium isothiocyanate tissue lysis followed by acid phenol extraction (Chomczynaki and Sacchi, *Anal. Biochem.*, 1987, 162:156). Northern analysis was performed using 6% formaldehyde-1. 96 agarose denaturing gel electrophoresis was performed as described in Maniatis et al. (SUPRA). RNAs were capillarily transferred and cross-linked to Zeta-Probe nylon membranes and were then prehybridized, hybridized, and washed according to the membrane manufacturer's specifications (Biorad Chemical Division, Richmond, Calif.)) and yielded a panel of macula-specific clones. The message corresponding to this cDNA was identified in 1 µg of sunfish saccular macula (SM) total RNA as a single transcript nearly 2.0 kb in length. A similar message was not detected in 2 µg samples of sunfish gill (G), heart (H), pars superior (PS=vestibular portion of ear), retina (R), brain (B), or liver (L). The blot was stripped and rehybridized to a cytoplasmic β-actin probe to confirm RNA integrity. In addition, no detectable expression of this gene was observed in 1 µg of poly-A+ RNA from sunfish brain, liver, or muscle.

Example 3

Analysis of the Saccular Collagen Gene

The complete nucleotide as well as the predicted amino acid sequence corresponding to the primary open reading frame of the cDNA have been determined (SEQ ID NO:1). The translated amino acid sequence of the 1269 nucleotide primary open reading frame (shown beneath the nucleic acid sequence and in SEQ ID NO:2) was found to encode a 423 amino acid structural protein containing a single 217 amino acid collagenous domain (amino acid positions 58–274 flanked by a 57 amino acid amino-terminal non-collagenous domain and a 149 amino acid carboxy-terminal non-collagenous domain. The collagenous domain contains 71 Gly-X-Y repeats with two minor imperfections (one Gly-X-Y-X-Y-Gly-x-Y and one Gly-X-Gly-X-Y) and has a 12 proline and an 8% lysine content. One potential N-linked glycosylation site is identified in each non-collagenous domain. The carboxy-terminal non-collagenous domain contains a region that is highly homologous to the carboxy terminal non-collagenous domains of the type VIII and the type X collagen. The 95 amino acid representing the C-terminal non-collagenous domain was found to contain an average of 40% identity and 56% overall homology at the amino acid level with the type VIII and type X sequences in any of the species in which these genes have been identified. This region of homology is also shared with the C1q complement proteins (Reid and Day, *Immunol. Today*, 1990, 11:387; Brass et al., *Febs Lett.*, 1992, 303:126). The amino-terminal non-collagenous domain displays no homology with any sequences reported to date. The first 19 amino acids of the amino terminal non-collagenous domain represent a putative signal peptide.

Collagen type X and VIII (Yamaguchi et al., *J. Biol. Chem.*, 1991, 266:4508; Yamagiuchi et al., *J. Biol. Chem.*, 1989, 264:16022; Ninomlya et al., *J. Biol. Chem.*, 1986, 261:5041; Muragaki et al., *J. Biol. Chem.*, 1991, 266:7721; and LuValle et al., *J. Biol. Chem.*, 1988, 263:18378) and this saccular collagen are distinguished by several features. First, they share a common domain organization: a single, relatively short collagenous domain separating small amino and carboxy terminal non-collagenous (NC) globular domains resulting in a dumbbell shaped molecule. They also share the related stretch of amino acids in each of their respective carboxy terminal NC domains mentioned above. In addition, each possesses a unique amino terminal NC domain that is not related to any sequences reported to date. This macular collagen is, therefore, a novel member of this family of short chain vertebrate collagen. The most distinguishing feature of this macular collagen is that it possesses a collagenous domain of only about half of the length of the collagenous domains in the type VIII and X collagen.

Example 4

In Situ Hybridization

Non radioactive in situ hybridization was used to deduce the localization of this gene's expression within the sunfish saccular epithelium. Serial 5 micron thick sections of Bouin's-fixed, paraffin-embedded saccular maculae were pre-treated, hybridized with antisense and sense digoxigenin labeled RNA probes specific to portions of the 3' end of the gene (none of the collagen domain coding sequence was included).

The resultant DIG-RNA/tissue mRNA hybrids were detected using an alkaline phosphatase conjugated anti-digoxigenin antibody. A cDNA containing 585 nucleotides of the 3' end of the macular collagen was obtained and band purified. The more 5' of the two fragments obtained by SacI digestion of this fragment was cloned into EcoRI/SacI digested pBluescript (Stratagene Cloning Systems, La Jolla, Calif.). Microgram quantities of a construct containing this fragment (none of the collagen encoding domain was included) were linearized to completion separately with an appropriate restriction enzyme that digested each end of the cDNA insert. SacI digested versions were treated with Klenow to create blunt ends at these 3' overhangs before riboprobe synthesis. All restriction and modifying enzymes were from BMB, Inc. and were used according to standard protocols (Maniatis et al., SUPRA). Digoxigenin (DIG)-labeled RNAs were synthesized using the Genius Labeling kit (Boehringer Mannheim Biochemical, Inc. (BMB), Indianapolis, Ind.). Non-radioactive in situ hybridization was performed using the Genius Nonradioactive Labeling and Detection System (BMB, Inc., Indianapolis, Ind.). Details of in situ hybridization protocols not itemized were closely parallel than those previously detailed (Simmons et al., *J. Histotechnology*, 1989, 12:169), whereas optimization of the immunodetection of DIG-RNA/tissue mRNA hybrids were based on several versions already reported for use with nonradioactive probes (Fisher et al., *J. Dermatol.*, 1991, 125:516; Springer et al., *J. Histochem. Cytochem.*, 1991, 39:231). Retained DIG-RNA/tissue cDNA hybrids were detected using alkaline phosphatase conjugated anti-digoxigenin Fab fragments and X-phosphate/NBT substrate based colorimetric development according to the manufacturer's specifications as previously optimized (Fisher et al., *J. Dermatol.*, 1991, 125:516). The in situ hybridizations may be photographed at approximately 100–200 X using 100-ASA Kodak color film. Transcripts encoding this protein were localized to the edges of the saccular epithelium whereas sections hybridized with a control probe showed only light, diffuse background staining. The corresponding hematoxylin and eosin stained section indicated that this expression was restricted to a group of specialized secretory supporting cells that reside around the edges of the saccular epithelium.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1839 base pairs
        ( B ) TYPE: nucleic acid
        ( C ) STRANDEDNESS: double
        ( D ) TOPOLOGY: both ( i i ) MOLECULE TYPE: cDNA ( i x ) FEATURE:
        ( A ) NAME/KEY: CDS
        ( B ) LOCATION: 331..1602

( x i ) SEQUENCE DESCRIPTION: SEQ ID NO:1:

```
CCTCTGAAGG TTCCAGAATC GATAGTGAAT TCGTGGACTA GTTGGAGAGG ATGGAATGAA      60

GAGTCAACAC AGGCTACACC TGCAGATTAT TGTGTCAAGC CCTCAGTATG CTGTCCATTC     120

GTCTAGTCTT CCTGACTGCT CTTCTTGTGG TACTGATGGC TGTGCTGACC TCCAGCACCA     180

GAACCACACG ATGGCCCAAA CCTCAGACAA CCAAGAAGCC TCCTCGAGCT GGGAGCAGCG     240

TGGAGGTGGG GTGGAGGATT CAAACGGACC ACTACCACCA CCCCATCTCC TACCAGTAGC     300

CTGCACACAG ACGAGACAAC TGAGGTTATG ATG GAC GCT TAC TCC TTG TCC CCT     354
                                 Met Asp Ala Tyr Ser Leu Ser Pro
                                  1               5

ACA GAC AGC ACC ACC TAC TCC AGC GAC ACT TTC TCC ACC GAG TTC CAC     402
Thr Asp Ser Thr Thr Tyr Ser Ser Asp Thr Phe Ser Thr Glu Phe His
         10              15                  20

ACC GAT GCC ATA GCG CCC CCT GGC AAC ACC CCT GGA AAC TAT ACC CTT     450
Thr Asp Ala Ile Ala Pro Pro Gly Asn Thr Pro Gly Asn Tyr Thr Leu
 25              30                  35                  40

GAT TAT AAT GAA TGC TTC TTC AAC TTC TGT GAG TGC TGT CCA CCA GAG     498
Asp Tyr Asn Glu Cys Phe Phe Asn Phe Cys Glu Cys Cys Pro Pro Glu
                 45                  50                  55

AAA GGC CCC ATG GGG CCC ATG GGA GAG AGA GGG CTG CCA GGA CCG CCA     546
Lys Gly Pro Met Gly Pro Met Gly Glu Arg Gly Leu Pro Gly Pro Pro
```

-continued

|  |  |  | 60 |  |  |  | 65 |  |  |  | 70 |  |  |  |  |
|---|---|---|---|---|---|---|---|---|---|---|---|---|---|---|---|
| GGA | GAG | AGG | GGT | CCT | CTA | GGG | TTA | CCA | GGG | GAG | AAG | GGA | GAG | ACA | GGG | 594 |
| Gly | Glu | Arg<br>75 | Gly | Pro | Leu | Gly | Leu<br>80 | Pro | Gly | Glu | Lys | Gly<br>85 | Glu | Thr | Gly |  |
| CTC | AGA | GGA | CCT | CCA | GGA | CCA | GCA | GGT | CTA | CCT | GGA | GCC | AAT | GGA | CTC | 642 |
| Leu | Arg<br>90 | Gly | Pro | Pro | Gly | Pro<br>95 | Ala | Gly | Leu | Pro | Gly<br>100 | Ala | Asn | Gly | Leu |  |
| AAT | GGC | GAC | ATA | GGT | GAA | AAA | GGT | GAT | CAA | GGA | CCG | GTG | GGT | CTT | CCT | 690 |
| Asn<br>105 | Gly | Asp | Ile | Gly<br>110 | Glu | Lys | Gly | Asp | Gln<br>115 | Gly | Pro | Val | Gly<br>120 | Leu | Pro |  |
| GGT | GTC | CCT | GGG | ATC | CCA | GGA | AAA | CCA | GGA | GAG | AAA | GGT | GAT | CCA | GGC | 738 |
| Gly | Val | Pro | Gly | Ile<br>125 | Pro | Gly | Lys | Pro | Gly<br>130 | Glu | Lys | Gly | Asp | Pro<br>135 | Gly |  |
| CTC | AAA | GGA | GAT | AAA | GGT | GAA | CGT | GGC | TTC | AGT | GGT | CTG | AAA | GGG | GAC | 786 |
| Leu | Lys | Gly | Asp<br>140 | Lys | Gly | Glu | Arg | Gly<br>145 | Phe | Ser | Gly | Leu | Lys<br>150 | Gly | Asp |  |
| CCG | GGA | GAA | AGA | GGA | GAG | CCT | GGC | CTA | AAT | GGA | ACT | AAA | GGA | AGC | ATC | 834 |
| Pro | Gly | Glu<br>155 | Arg | Gly | Glu | Pro | Gly<br>160 | Leu | Asn | Gly | Thr | Lys<br>165 | Gly | Ser | Ile |  |
| GGG | CGA | GAG | GGG | CCC | ATG | GGT | CCT | GGG | TTA | GCT | GGG | ACA | AAG | GGT | CTG | 882 |
| Gly | Arg<br>170 | Glu | Gly | Pro | Met<br>175 | Gly | Pro | Gly | Leu | Ala<br>180 | Gly | Thr | Lys | Gly | Leu |  |
| AAA | GGT | GAA | CAG | GGG | CTT | AAA | GGC | GAG | TGT | TTA | CAA | GGC | GAG | AAA | GGT | 930 |
| Lys<br>185 | Gly | Glu | Gln | Gly<br>190 | Leu | Lys | Gly | Glu | Cys<br>195 | Leu | Gln | Gly | Glu | Lys<br>200 | Gly |  |
| GAG | CGT | GGG | CCC | CCT | GGT | TTG | AGA | GGT | GAG | ATG | GGA | TTG | AAT | GGA | ACT | 978 |
| Glu | Arg | Gly | Pro | Pro<br>205 | Gly | Leu | Arg | Gly | Glu<br>210 | Met | Gly | Leu | Asn | Gly<br>215 | Thr |  |
| GAT | GGT | GTA | AAG | GGA | GAG | AGA | GGG | GAG | CCA | GGG | CCT | CTT | GGA | GGG | AAG | 1026 |
| Asp | Gly | Val | Lys<br>220 | Gly | Glu | Arg | Gly | Glu<br>225 | Pro | Gly | Pro | Leu | Gly<br>230 | Gly | Lys |  |
| GGG | GAT | ACT | GGT | GCC | AGA | GGG | CCC | CCA | GGT | CCT | CCA | GGA | GGG | AGG | GGC | 1074 |
| Gly | Asp | Thr<br>235 | Gly | Ala | Arg | Gly | Pro<br>240 | Pro | Gly | Pro | Pro | Gly<br>245 | Gly | Arg | Gly |  |
| ATG | GCA | GGG | TTG | AGG | GGG | GAG | AAG | GGG | CTT | AAA | GGT | GTG | CGT | GGG | CCA | 1122 |
| Met | Ala<br>250 | Gly | Leu | Arg | Gly | Glu<br>255 | Lys | Gly | Leu | Lys | Gly<br>260 | Val | Arg | Gly | Pro |  |
| AGG | GGC | CCT | AAA | GGC | CCA | CCA | GGT | GAG | AGT | GTG | GAG | CAG | ATT | CGC | TCT | 1170 |
| Arg<br>265 | Gly | Pro | Lys | Gly<br>270 | Pro | Pro | Gly | Glu | Ser<br>275 | Val | Glu | Gln | Ile | Arg<br>280 | Ser |  |
| GCT | TTC | AGT | GTG | GGC | TTG | TTC | CCG | AGC | AGA | TCC | TTC | CCT | CCG | CCC | AGC | 1218 |
| Ala | Phe | Ser | Val<br>285 | Gly | Leu | Phe | Pro | Ser<br>290 | Arg | Ser | Phe | Pro | Pro<br>295 | Pro | Ser |  |
| CTG | CCT | GTG | AAG | TTT | GAT | AAG | GTG | TTT | TAC | AAC | GGG | GAG | GGG | CAC | TGG | 1266 |
| Leu | Pro | Val | Lys<br>300 | Phe | Asp | Lys | Val | Phe<br>305 | Tyr | Asn | Gly | Glu | Gly<br>310 | His | Trp |  |
| GAC | CCA | ACA | CTC | AAC | AAA | TTC | AAT | GTC | ACC | TAC | CCG | GGG | GTC | TAC | CTA | 1314 |
| Asp | Pro | Thr<br>315 | Leu | Asn | Lys | Phe | Asn<br>320 | Val | Thr | Tyr | Pro | Gly<br>325 | Val | Tyr | Leu |  |
| TTC | AGT | TAC | CAC | ATC | ACC | GTG | CGC | AAC | AGG | CCT | GTG | CGT | GCT | GCC | CTA | 1362 |
| Phe | Ser | Tyr<br>330 | His | Ile | Thr | Val<br>335 | Arg | Asn | Arg | Pro | Val<br>340 | Arg | Ala | Ala | Leu |  |
| GTG | GTT | AAT | GGG | GTA | CGG | AAG | CTG | AGG | ACC | CGG | GAT | TCT | CTG | TAC | GGC | 1410 |
| Val | Val | Asn | Gly<br>345 | Val | Arg | Lys | Leu | Arg<br>350 | Thr | Arg | Asp | Ser | Leu<br>355 | Tyr | Gly |  |
| CAG | GAC | ATC | GAT | CAG | GCG | TCC | AAC | CTC | GCA | CTG | CTG | CAT | CTG | ACT | GAC | 1458 |
| Gln | Asp | Ile | Asp | Gln<br>365 | Ala | Ser | Asn | Leu | Ala<br>370 | Leu | Leu | His | Leu | Thr<br>375 | Asp |  |
| GGT | GAC | CAG | GTG | TGG | CTG | GAG | ACA | CTG | AGA | GAC | TGG | AAT | GGA | GTT | ACT | 1506 |
| Gly | Asp | Gln | Val | Trp | Leu | Glu | Thr | Leu | Arg | Asp | Trp | Asn | Gly | Val | Thr |  |

-continued

|  |  | 380 |  |  |  |  | 385 |  |  |  |  | 390 |  |  |  |
|---|---|---|---|---|---|---|---|---|---|---|---|---|---|---|---|
| CCA | GCA | GTG | AGG | ATG | ACA | GCA | CTT | TCT | CTG | GCT | TCT | TGC | TTT | ACC | CTG | 1554 |
| Pro | Ala | Val | Arg | Met | Thr | Ala | Leu | Ser | Leu | Ala | Ser | Cys | Phe | Thr | Leu |  |
|  |  | 395 |  |  |  |  | 400 |  |  |  |  | 405 |  |  |  |  |
| ACA | CAA | AGA | AAC | CTA | CTG | CTA | TGG | AAA | ACC | TGT | GAA | GGC | AAA | CTT | TAA | 1602 |
| Thr | Gln | Arg | Asn | Leu | Leu | Leu | Trp | Lys | Thr | Cys | Glu | Gly | Lys | Leu |  |  |
|  |  | 410 |  |  |  |  | 415 |  |  |  |  | 420 |  |  |  |  |

CCTTGAATGA GCTCTGATTG TAACTTCCTG TATACTCTGC ACAACCTTCA GCCTATTGCA 1662
CTGCTCTGTG AAATTAATGT GTTTCAGCTT AATACTGCTG CTTCAGTATC TATCGTGTTA 1722
ATCAAACCAG AATGCTTTGC TTGCCCTACT GTATTTGAAG ATGGACAAGG CTTGATTATA 1782
GTGCTGTATG CAACCCTTCA GTTCTTTGTA ACAATGCATT AAAAATGACT ACGCTTG 1839

( 2 ) INFORMATION FOR SEQ ID NO:2:

( i ) SEQUENCE CHARACTERISTICS:
( A ) LENGTH: 423 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Met | Asp | Ala | Tyr | Ser | Leu | Ser | Pro | Thr | Asp | Ser | Thr | Thr | Tyr | Ser | Ser |
|---|---|---|---|---|---|---|---|---|---|---|---|---|---|---|---|
| 1 |  |  |  | 5 |  |  |  |  | 10 |  |  |  |  | 15 |  |

| Asp | Thr | Phe | Ser | Thr | Glu | Phe | His | Thr | Asp | Ala | Ile | Ala | Pro | Pro | Gly |
|---|---|---|---|---|---|---|---|---|---|---|---|---|---|---|---|
|  |  |  | 20 |  |  |  |  | 25 |  |  |  |  | 30 |  |  |

| Asn | Thr | Pro | Gly | Asn | Tyr | Thr | Leu | Asp | Tyr | Asn | Glu | Cys | Phe | Phe | Asn |
|---|---|---|---|---|---|---|---|---|---|---|---|---|---|---|---|
|  |  | 35 |  |  |  |  | 40 |  |  |  |  | 45 |  |  |  |

| Phe | Cys | Glu | Cys | Cys | Pro | Pro | Glu | Lys | Gly | Pro | Met | Gly | Pro | Met | Gly |
|---|---|---|---|---|---|---|---|---|---|---|---|---|---|---|---|
|  | 50 |  |  |  |  | 55 |  |  |  |  | 60 |  |  |  |  |

| Glu | Arg | Gly | Leu | Pro | Gly | Pro | Pro | Gly | Glu | Arg | Gly | Pro | Leu | Gly | Leu |
|---|---|---|---|---|---|---|---|---|---|---|---|---|---|---|---|
| 65 |  |  |  |  | 70 |  |  |  |  | 75 |  |  |  |  | 80 |

| Pro | Gly | Glu | Lys | Gly | Glu | Thr | Gly | Leu | Arg | Gly | Pro | Pro | Gly | Pro | Ala |
|---|---|---|---|---|---|---|---|---|---|---|---|---|---|---|---|
|  |  |  |  | 85 |  |  |  |  | 90 |  |  |  |  | 95 |  |

| Gly | Leu | Pro | Gly | Ala | Asn | Gly | Leu | Asn | Gly | Asp | Ile | Gly | Glu | Lys | Gly |
|---|---|---|---|---|---|---|---|---|---|---|---|---|---|---|---|
|  |  |  | 100 |  |  |  |  | 105 |  |  |  |  | 110 |  |  |

| Asp | Gln | Gly | Pro | Val | Gly | Leu | Pro | Gly | Val | Pro | Gly | Ile | Pro | Gly | Lys |
|---|---|---|---|---|---|---|---|---|---|---|---|---|---|---|---|
|  |  | 115 |  |  |  |  | 120 |  |  |  |  | 125 |  |  |  |

| Pro | Gly | Glu | Lys | Gly | Asp | Pro | Gly | Leu | Lys | Gly | Asp | Lys | Gly | Glu | Arg |
|---|---|---|---|---|---|---|---|---|---|---|---|---|---|---|---|
|  | 130 |  |  |  |  | 135 |  |  |  |  | 140 |  |  |  |  |

| Gly | Phe | Ser | Gly | Leu | Lys | Gly | Asp | Pro | Gly | Glu | Arg | Gly | Glu | Pro | Gly |
|---|---|---|---|---|---|---|---|---|---|---|---|---|---|---|---|
| 145 |  |  |  |  | 150 |  |  |  |  | 155 |  |  |  |  | 160 |

| Leu | Asn | Gly | Thr | Lys | Gly | Ser | Ile | Gly | Arg | Glu | Gly | Pro | Met | Gly | Pro |
|---|---|---|---|---|---|---|---|---|---|---|---|---|---|---|---|
|  |  |  |  | 165 |  |  |  |  | 170 |  |  |  |  | 175 |  |

| Gly | Leu | Ala | Gly | Thr | Lys | Gly | Leu | Lys | Gly | Glu | Gln | Gly | Leu | Lys | Gly |
|---|---|---|---|---|---|---|---|---|---|---|---|---|---|---|---|
|  |  |  | 180 |  |  |  |  | 185 |  |  |  |  | 190 |  |  |

| Glu | Cys | Leu | Gln | Gly | Glu | Lys | Gly | Glu | Arg | Gly | Pro | Pro | Gly | Leu | Arg |
|---|---|---|---|---|---|---|---|---|---|---|---|---|---|---|---|
|  |  | 195 |  |  |  |  | 200 |  |  |  |  | 205 |  |  |  |

| Gly | Glu | Met | Gly | Leu | Asn | Gly | Thr | Asp | Gly | Val | Lys | Gly | Glu | Arg | Gly |
|---|---|---|---|---|---|---|---|---|---|---|---|---|---|---|---|
|  | 210 |  |  |  |  | 215 |  |  |  |  | 220 |  |  |  |  |

| Glu | Pro | Gly | Pro | Leu | Gly | Gly | Lys | Gly | Asp | Thr | Gly | Ala | Arg | Gly | Pro |
|---|---|---|---|---|---|---|---|---|---|---|---|---|---|---|---|
| 225 |  |  |  |  | 230 |  |  |  |  | 235 |  |  |  |  | 240 |

| Pro | Gly | Pro | Pro | Gly | Gly | Arg | Gly | Met | Ala | Gly | Leu | Arg | Gly | Glu | Lys |
|---|---|---|---|---|---|---|---|---|---|---|---|---|---|---|---|
|  |  |  |  | 245 |  |  |  |  | 250 |  |  |  |  | 255 |  |

| Gly | Leu | Lys | Gly | Val | Arg | Gly | Pro | Arg | Gly | Pro | Lys | Gly | Pro | Pro | Gly |
|---|---|---|---|---|---|---|---|---|---|---|---|---|---|---|---|
|  |  |  | 260 |  |  |  |  | 265 |  |  |  |  | 270 |  |  |

| | | | | | | | | | | | | | | |
|---|---|---|---|---|---|---|---|---|---|---|---|---|---|---|
| Glu | Ser | Val<br>275 | Glu | Gln | Ile | Arg | Ser<br>280 | Ala | Phe | Ser | Val | Gly<br>285 | Leu | Phe | Pro |
| Ser | Arg<br>290 | Ser | Phe | Pro | Pro | Pro<br>295 | Ser | Leu | Pro | Val | Lys<br>300 | Phe | Asp | Lys | Val |
| Phe<br>305 | Tyr | Asn | Gly | Glu | Gly<br>310 | His | Trp | Asp | Pro | Thr<br>315 | Leu | Asn | Lys | Phe | Asn<br>320 |
| Val | Thr | Tyr | Pro | Gly<br>325 | Val | Tyr | Leu | Phe | Ser<br>330 | Tyr | His | Ile | Thr | Val<br>335 | Arg |
| Asn | Arg | Pro | Val<br>340 | Arg | Ala | Ala | Leu | Val<br>345 | Val | Asn | Gly | Val | Arg<br>350 | Lys | Leu |
| Arg | Thr | Arg<br>355 | Asp | Ser | Leu | Tyr | Gly<br>360 | Gln | Asp | Ile | Asp | Gln<br>365 | Ala | Ser | Asn |
| Leu | Ala<br>370 | Leu | Leu | His | Leu | Thr<br>375 | Asp | Gly | Asp | Gln | Val<br>380 | Trp | Leu | Glu | Thr |
| Leu<br>385 | Arg | Asp | Trp | Asn | Gly<br>390 | Val | Thr | Pro | Ala | Val<br>395 | Arg | Met | Thr | Ala | Leu<br>400 |
| Ser | Leu | Ala | Ser | Cys<br>405 | Phe | Thr | Leu | Thr | Gln<br>410 | Arg | Asn | Leu | Leu | Leu<br>415 | Trp |
| Lys | Thr | Cys | Glu<br>420 | Gly | Lys | Leu | | | | | | | | | |

We claim:

1. An isolated nucleic acid molecule comprising a nucleotide sequence that encodes the protein having the amino acid sequence of SEQ ID NO:2.

2. The isolated nucleic acid molecule of claim 1 comprising SEQ ID NO:1.

3. A recombinant expression vector comprising a nucleotide sequence that encodes the protein having the amino acid sequence of SEQ ID NO:2.

4. The recombinant expression vector of claim 3 wherein the vector further comprises a mammary-specific promoter.

5. The recombinant expression vector of claim 3 wherein the nucleic acid sequence comprises SEQ ID NO:1.

6. The recombinant expression vector of claim 5 wherein the vector further comprises a mammary-specific promoter.

7. A host cell comprising the recombinant expression vector of claim 3.

8. The host cell of claim 7 wherein said host cell comprises a recombinant expression vector that comprises SEQ ID NO:1.

9. The host cell of claim 7 wherein the host cell is a prokaryotic cell.

10. The host cell of claim 7 wherein the host cell is a eukaryotic cell.

11. The eukaryotic host cell of claim 10, wherein the host cell is selected from the group consisting of mammalian cells, insect cells, and yeast cells.

12. An isolated oligonucleotide molecule comprising a nucleotide sequence complementary to a nucleotide sequence of at least 50 nucleotides of SEQ ID NO:1.

13. The oligonucleotide molecule of claim 12 wherein said oligonucleotide molecule is a fragment of SEQ ID NO:1.

14. The oligonucleotide molecule of claim 12 wherein said oligonucleotide molecule comprises a nucleotide sequence complementary to a nucleotide sequence of at least 100 nucleotides of SEQ ID NO:1.

15. The oligonucleotide molecule of claim 14 wherein said oligonucleotide molecule is a fragment of SEQ ID NO:1.

16. An oligonucleotide molecule comprising a nucleotide sequence complementary to a nucleotide sequence of at least 10 nucleotides of SEQ ID NO:1 between nucleotide 331 and nucleotide 501 of SEQ ID NO:1, or between nucleotide 1600 and nucleotide 1839 of SEQ ID NO:1.

17. The oligonucleotide molecule of claim 16 wherein said oligonucleotide molecule is a fragment of SEQ ID NO:1.

18. The oligonucleotide molecule of claim 16 wherein said oligonucleotide molecule comprises a nucleotide sequence complementary to a nucleotide sequence of 15–150 nucleotides of SEQ ID NO:1.

19. The oligonucleotide molecule of claim 18 wherein said oligonucleotide molecule is a fragment of SEQ ID NO:1.

20. The oligonucleotide molecule of claim 16 wherein said oligonucleotide molecule comprises a nucleotide sequence complementary to a nucleotide sequence of at least 15–30 nucleotides of SEQ ID NO:1.

21. The oligonucleotide molecule of claim 20 wherein said oligonucleotide molecule is a fragment of SEQ ID NO:1.

22. The oligonucleotide molecule of claim 16 wherein said oligonucleotide molecule is a fragment of SEQ ID NO:1 consisting of nucleotides 331–501 of SEQ ID NO:1.

23. The oligonucleotide molecule of claim 16 wherein said oligonuleotide molecule is a fragment of SEQ ID NO:1 consisting of nucleotides 1600–1839 of SEQ ID NO:1.

* * * * *